(12) United States Patent
O'Brien et al.

(10) Patent No.: US 6,559,124 B1
(45) Date of Patent: *May 6, 2003

(54) USE OF PROSAPOSIN AND PEPTIDES OBTAINED THEREFROM FOR TREATMENT OF NEURAL DEGENERATION

(75) Inventors: John S. O'Brien, San Diego, CA (US); Yasuo Kishimoto, San Diego, CA (US)

(73) Assignee: Myelos Corporation, Iselin, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/076,258

(22) Filed: May 12, 1998

Related U.S. Application Data

(60) Continuation of application No. 08/958,970, filed on Oct. 28, 1997, now abandoned, which is a continuation of application No. 08/483,146, filed on Jun. 7, 1995, now Pat. No. 5,696,080, which is a division of application No. 08/100,247, filed on Jul. 30, 1993, now Pat. No. 5,571,787.

(51) Int. Cl.[7] ............................................. A61K 38/18
(52) U.S. Cl. ........................ 514/12; 514/13; 424/185.1
(58) Field of Search ................... 514/12, 13; 424/185.1

(56) References Cited

U.S. PATENT DOCUMENTS

| | | | |
|---|---|---|---|
| 5,470,582 A | | 11/1995 | Supersaxo et al. .......... 424/489 |
| 5,714,459 A | * | 2/1998 | O'Brien et al. ................ 514/2 |

FOREIGN PATENT DOCUMENTS

| | | |
|---|---|---|
| WO | 9311238 | 6/1993 |

OTHER PUBLICATIONS

Jackowski British J. Neurosurgery 9: 303–317, 1995.*
Prapp "Retinal Phototoxicity", In "Handbook of Neurotoxicity" (ed. L.W. Chang et al) Marcel Dekker, Inc. New York pp. 963–1003, 1995.*
Kotani Y. et al., "Prosaposin facilitates sciatic nerve regeneration in vivo," Neurochem 66(5) (1996), pp. 2019–2025.
Aderka, D. et al., IL–6 inhibits lipopolysaccharide–induced tumor necrosis factor production . . . Jour. of Immunol. 143(11):3517–3523 (1989).
Banks, W., et al. Permeability of the blood–brain barrier to peptides: an approach . . . Peptides 13:1289–1294 (1992).
Barde, Y.A. Trophic factors and neuronal survival. Neuron 1:1525–1534 (1989).
Baringe, M. Neurotrophic factors enter the clinic. Science 264:772–774 (1994).
Bazan, J. Neuropoietic cytokines in the hematopoietic fold. Neuron 7:197–208, (1991).
Bradová, V. et al. Prosaposin deficiency: further characterization of the sphingolipid activator protein–deficient sibs. Human Genetics 92:143–152 (1993).
Dewji, N. et al., Nucleotide sequence of cloned cDNA for human sphingolipid activator . . . Proc. Natl. Acad. Sci. USA, 84:8652–8656 (1987).
Dewji, N. et al., Molecular cloning of the sphingolipid activator protein . . . Biochem. and Biophys. Res. Commun. 134(2):989–994 (1986).
Fonnum, A rapid radiochemical method for the determination of choline acetyltransferase . . . Jour. of Neurochemistry 24:407–409 (1975).
Francis, M. et al., Immunological properties of hepatitis B core antigen fusion proteins. Proc. Natl. Acad. Sci. 87:2545–2549 (1990).
Fürst, W. et al., The complete amino–acid sequences of human ganglioside GM2 activator protein and cerebroside sulfate activator protein. Eur. J. Biochem. 192:709–714 (1990).
Gurney, M. et al., Induction of motor neuron sprouting in vivo by ciliary neurotrophic factor and basic fibroblast growth factor. Jour. of Neuroscience 12(8):3241–3247 (1992).
Hefti, F. et al., Function of neurotrophic factors in the adult and aging brain . . . Neurobiology of Aging 10:515–533 (1989).
Henderson, C. et al., Neurotrophic factors in development and plasticity of spinal neurons. Restorative Neurology and Neuroscience 5:15–28 (1993).
Hiraiwa, M. et al., Binding and transport of gangliosides by prosaposin. Proc. Natl. Acad. Sci. USA, 89:11254–11258 (1992).
Hiraiwa, M. et al., Isolation, characterization, and proteolysis of human prosaposin . . . Arch. Biochem. Biophys. 304(1)110–116 (1993).
Hofer, M. et al., Brain–derived neurotrophic factor prevents neuronal death in vivo. Nature 331:261–262 (1988).
Ip, N. et al., The neurotrophins and CNTP: specificity of action toward PNS and CNS neurons. J. Physiol., 85:123–130 (1991).
Kishimoto, Y. et al., Saposins: structure, function, distribution, and molecular genetics. Jour. of Lipid Research, 3:1255–1268 (1992).
Kleinschmidt, T. et al. Complete amino–acid sequence and carbohydrate content of the naturally occurring glucosylceramide activator protein . . . Biological Chemistry Hoppe-Seyler 368(12):1573–1578 (1987).
Kondoh, K. et al. Distribution of prosaposin–like immunoreactivity in rat brain. Jour. of Comparative Neurology 334:590–602 (1993).
Kondoh, K. et al. Isolation and characterization of prosaposin from human milk. Biochem. and Biophys. Res. Commun. 181(1):286–292 (1991).

(List continued on next page.)

*Primary Examiner*—Gary Kunz
*Assistant Examiner*—Robert C. Hayes
(74) *Attorney, Agent, or Firm*—Kenyon & Kenyon

(57) ABSTRACT

Prosaposin, saposin C and various peptide fragments of saposin C stimulate neurite outgrowth in vitro. In addition, prosaposin and saposin C promote increased myelination ex vivo. Prosaposin is present in large neurons of the brain, including both upper and lower motor neurons.

4 Claims, 4 Drawing Sheets

OTHER PUBLICATIONS

Krystal, G. A simple microassay for erythropoietin based on 3H–thymidine incorporation . . . Exp. Hematol. 11(7):649–660 (1983).

Kwon, Y. et al., Systemic injections of ciliary neurotrophic factor induce sprouting by adult motor neurons. Neuroreport 5:789–792 (1994).

Lamontagne, S. et al. Modulation of human saposin B sphingolipid–binding specificity by alternative splicing. Jour. of Biol. Chem. 269:20528–20532 (1994).

Lin, L. et al., Purification, cloning, and expression of ciliary neurotrophic factor (CNTF). Science 246:1023–1025, (1989).

Lindsay, R. et al., The neurotrophin family of NGF–related neurotrophic factors. Restorative Neurology and Neuroscience 2:211–220 (1991).

Maisonpierre, P. et al., Neurotrophin–3: a neurotrophic factor related to NGF and BDNF. Science, 247:1446–1451 (1990).

Morimoto, S. et al., Distribution of saposin proteins (sphingolipid . . . ). Proc. Natl. Acad. Sci. USA, 87:3493–3497 (1990).

Morimoto, S. et al., Saposin A: Second cerebrosidase activator protein. Proc. Natl. Acad. Sci. 86:3389–3393 (1989).

Morimoto, S. et al., Saposin D: A sphingomyelinase activator. Biochemical and Biophysical Research Communications 156(1):403–410 (1988).

O'Brien, J. et al., Identification of prosaposin as a neurotrophic factor. Proc. Natl. Acad. Sci. 91(20):9593–9596 (1994).

O'Brien, J. et al., Isolation and characterization of prosaposin . . . FASEB Jour. 6(4):A969 (1992).

O'Brien, J. et al., Saposin proteins: structure, function, and role in human lysosomal . . . FASEB Jour. 5:301–308 (1991).

O'Brien, J. et al., Coding of two sphingolipid activator proteins (SAP–1 and SAP–2) . . . Science 241:1098–1101 (1988).

Priestle, J.P. et al., Crystallographic refinement of interleukin . . . Proc. Natl. Acad. Sci. 86:9667–9671 (1989).

Purves, D. et al., Trophic regulation of nerve cell morphology and innervation . . . Nature, 336:123–128 (1988).

Rich, K. et al., Nerve growth factor protects adult sensory neurons from cell death . . . Jour. of Neurocytology 16:261–268 (1987).

Rorman, E. et al., Structure and evolution of the human prosaposin chromosomal gene. Genomics 12(2):312–318 (1992).

Sano, A. et al., Protection by prosaposin against ischemia–induced learining disability and neuronal loss. Biochem. and Biophys. Res. Commun. 204(2):994–1000 (1994).

Sano, A. et al., Saposin–C from bovine spleen; complete amino acid sequence and relation between the structure and its biological activity. Biochim. et Biophys. Acta 1120(1):75–80 (1991).

Satomi, D. Developmental changes of glutamate decarboxylase and 2',3'–cyclic nucleotide . . . Zoological Science 9:127–132 (1992).

Soeda, S. et al., Binding of cerebrosides and sulfatides to saposins A–D*. Jour. of Biol. Chem. 268(25):18519–18523 (1993).

Sprang, S. et al., Cytokine structural taxonomy and mechanisms of receptor engagement. Current Opinion in Structural Biology, 3:815–827 (1993).

Triguero, D. et al., Capillary depletion method for quantification of blood–brain barrier transport of circulating peptides and plasma proteins. J. of Neurochem., 54(6)1882–1888 (1990).

Nakano, T. et al., Structure of Full–Length cDNA Coding for Sulfatide Activator, a Co–β–Glucosidase and Two Other Homologous Proteins . . . J. Biochem., 105:152–154 (1989).

Remington's Pharmaceutical Sciences, 18th ed., 1990, ed. A.R. Gennaro, Easton, PA, p. 1552–1553, 1878–1880.

* cited by examiner

```
         8                           18              29
HUMAN    C E F L V K E V T K L I D N K T E K E I L
MOUSE    C Q F V M N R K F S E L I V N A T E L L L
RAT      C Q L V N R K V M K L I I N A T E L K I Y
G. PIG   C E Y V V K K V V K L I D N R T E L I I .
BOVINE   C E F V V K E V A K L I D N R T E K I I L

CONSENSUS C . . V . . . . . . L I . N N . T E . . I (L)

7                    17                 28
SAPOSIN A C K D V V T A A G D M L K D N A T E E E I L
```

FIG. 2B

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:1:

Cys Glu Phe Leu Val Lys Glu Val Thr Lys Leu Ile Asp Asn Asn Lys
 1               5                  10                  15

Thr Glu Lys Glu Ile Leu
            20

(2) INFORMATION FOR SEQ ID NO:2:

(i) SEQUENCE CHARACTERISTICS:
        (A) LENGTH: 523 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:2:

Met Tyr Ala Leu Phe Leu Leu Ala Ser Leu Leu Gly Ala Ala Leu Ala
 1               5                  10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
            35                  40                  45

Leu Gln Thr Val Trp Asn Lys Pro Thr Val Lys Ser Leu Pro Cys Asp
     50                  55                  60

Ile Cys Lys Asp Val Val Thr Ala Ala Gly Asp Met Leu Lys Asp Asn
 65                  70                  75                  80

Ala Thr Glu Glu Glu Ile Leu Val Tyr Leu Glu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
            115                 120                 125

Gly Glu Val Cys Ser Ala Leu Asn Leu Cys Glu Ser Leu Gln Lys His
            130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

```
Asp Gly Asp Val Cys Gln Asp Cys Ile Gln Met Val Thr Asp Ile Gln
        195                 200                 205

Thr Ala Val Arg Thr Asn Ser Thr Phe Val Gln Ala Leu Val Glu His
        210                 215                 220

Val Lys Glu Glu Cys Asp Arg Leu Gly Pro Gly Met Ala Asp Ile Cys
225                 230                 235                 240

Lys Asn Tyr Ile Ser Gln Tyr Ser Glu Ile Ala Ile Gln Met Met Met
                245                 250                 255

His Met Gln Pro Lys Glu Ile Cys Ala Leu Val Gly Phe Cys Asp Glu
                260                 265                 270

Val Lys Glu Met Pro Met Gln Thr Leu Val Pro Ala Lys Val Ala Ser
        275                 280                 285

Lys Asn Val Ile Pro Ala Leu Asp Leu Val Asp Pro Ile Lys Lys His
        290                 295                 300

Glu Val Pro Ala Lys Ser Asp Val Tyr Cys Glu Val Cys Glu Phe Leu
305                 310                 315                 320

Val Lys Glu Val Thr Lys Leu Ile Asp Asn Asn Lys Thr Glu Lys Glu
                325                 330                 335

Ile Leu Asp Ala Phe Asp Lys Met Cys Ser Lys Leu Pro Lys Ser Leu
                340                 345                 350

Ser Glu Glu Cys Gln Glu Val Val Asp Thr Tyr Gly Ser Ser Ile Leu
        355                 360                 365

Ser Ile Leu Leu Glu Glu Val Ser Pro Glu Leu Val Cys Ser Met Leu
        370                 375                 380

His Leu Cys Ser Gly Thr Arg Leu Pro Ala Leu Thr Val His Val Thr
385                 390                 395                 400

Gln Pro Lys Asp Gly Phe Cys Glu Val Cys Lys Lys Leu Val Gly
                405                 410                 415

Thr Leu Asp Arg Asn Leu Glu Lys Asn Ser Thr Lys Gln Glu Ile Leu
                420                 425                 430

Ala Ala Leu Glu Lys Gly Cys Ser Phe Leu Pro Asp Pro Tyr Gln Lys
        435                 440                 445

Gln Cys Asp Gln Phe Val Ala Glu Tyr Glu Pro Val Leu Ile Glu Ile
        450                 455                 460

Leu Val Glu Val Met Asp Pro Ser Phe Val Cys Leu Lys Ile Gly Ala
465                 470                 475                 480

Cys Pro Ser Ala His Lys Pro Leu Leu Gly Thr Glu Lys Cys Ile Trp
                485                 490                 495

Gly Pro Ser Tyr Trp Cys Gln Asn Thr Glu Thr Ala Ala Gln Cys Asn
                500                 505                 510

Ala Val Glu His Cys Lys Arg His Val Trp Asn
        515                 520
```

(2) INFORMATION FOR SEQ ID NO:3:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:3:

Ser Asp Val Tyr Cys Glu Val Cys Glu Phe Leu Val Lys Glu Val Thr

-continued

```
  1               5                10                15
Lys Leu Ile Asp Asn Asn Lys Thr Glu Lys Glu Ile Leu Asp Ala Phe
             20                25                30
Asp Lys Met Cys Ser Lys Leu Pro Lys Ser Leu Ser Glu Glu Cys Gln
         35                40                45
Glu Val Val Asp Thr Tyr Gly Ser Ser Ile Leu Ser Ile Leu Leu Glu
     50                55                60
Glu Val Ser Pro Glu Leu Val Cys Ser Met Leu His Leu Cys Ser Gly
 65                70                75                80
```

(2) INFORMATION FOR SEQ ID NO:4:

(i) SEQUENCE CHARACTERISTICS:
        (A) LENGTH: 2740 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
ATGTACGCCC TCTTCCTCCT GGCCAGCCTC CTGGGCGCGG CTCTAGCCGG CCCGGTCCTT      60
GGACTGAAAG AATGCACCAG GGGCTCGGCA GTGTGGTGCC AGAATGTGAA GACGGCGTCC     120
GACTGCGGGG CAGTGAAGCA CTGCCTGCAG ACCGTTTGGA ACAAGCCAAC AGTGAAATCC     180
CTTCCCTGCG ACATATGCAA AGACGTTGTC ACCGCAGCTG GTGATATGCT GAAGGACAAT     240
GCCACTGAGG AGGAGATCCT TGTTTACTTG GAGAAGACCT GTGACTGGCT TCCGAAACCG     300
AACATGTCTG CTTCATGCAA GGAGATAGTG GACTCCTACC TCCCTGTCAT CCTGGACATC     360
ATTAAAGGAG AAATGAGCCG TCCTGGGGAG GTGTGCTCTG CTCTCAACCT CTGCGAGTCT     420
CTCCAGAAGC ACCTAGCAGA GCTGAATCAC CAGAAGCAGC TGGAGTCCAA TAAGATCCCA     480
GAGCTGGACA TGACTGAGGT GGTGGCCCCC TTCATGGCCA ACATCCCTCT CCTCCTCTAC     540
CCTCAGGACG GCCCCCGCAG CAAGCCCCAG CCAAAGGATA ATGGGGACGT TGCCAGGAC      600
TGCATTCAGA TGGTGACTGA CATCCAGACT GCTGTACGGA CCAACTCCAC CTTTGTCCAG     660
GCCTTGGTGG AACATGTCAA GGAGGAGTGT GACCGCCTGG GCCCTGGCAT GGCCGACATA     720
TGCAAGAACT ATATCAGCCA GTATTCTGAA ATTGCTATCC AGATGATGAT GCACATGCAA     780
CCCAAGGAGA TCTGTGCGCT GGTTGGGTTC TGTGATGAGG TGAAAGAGAT GCCCATGCAG     840
ACTCTGGTCC CCGCCAAAGT GGCCTCCAAG AATGTCATCC CTGCCCTGGA ACTGGTGGAG     900
CCCATTAAGA AGCACGAGGT CCCAGCAAAG TCTGATGTTT ACTGTGAGGT GTGTGAATTC     960
CTGGTGAAGG AGGTGACCAA GCTGATTGAC AACAACAAGA CTGAGAAAGA AATACTCGAC    1020
GCTTTTGACA AAATGTGCTC GAAGCTGCCG AAGTCCCTGT CGGAAGAGTG CCAGGAGGTG    1080
GTGGACACGT ACGGCAGCTC CATCCTGTCC ATCCTGCTGG AGGAGGTCAG CCCTGAGCTG    1140
GTGTGCAGCA TGCTGCACCT CTGCTCTGGC ACGCGGCTGC CTGCACTGAC CGTTCACGTG    1200
ACTCAGCCAA AGGACGGTGG CTTCTGCGAA GTGTGCAAGA AGCTGGTGGG TTATTTGGAT    1260
CGCAACCTGG AGAAAAACAG CACCAAGCAG GAGATCCTGG CTGCTCTTGA GAAAGGCTGC    1320
AGCTTCCTGC CAGACCCTTA CCAGAAGCAG TGTGATCAGT TTGTGGCAGA GTACGAGCCC    1380
GTGCTGATCG AGATCCTGGT GGAGGTGATG GATCCTTCCT TCGTGTGCTT GAAAATTGGA    1440
GCCTGCCCCT CGGCCCATAA GCCCTTGTTG GGAACTGAGA AGTGTATATG GGGCCCAAGC    1500
TACTGGTGCC AGAACACAGA GACAGCAGCC CAGTGCAATG CTGTCGAGCA TTGCAAACGC    1560
```

-continued

```
CATGTGTGGA ACTAGGAGGA GGAATATTCC ATCTTGGCAG AAACCACAGC ATTGGTTTTT    1620

TTCTACTTGT GTGTCTGGGG GAATGAACGC ACAGATCTGT TTGACTTTGT TATAAAAATA    1680

GGGCTCCCCC ACCTCCCCCA TTTCTGTGTC CTTTATTGTA GCATTGCTGT CTGCAAGGGA    1740

GCCCCTAGCC CCTGGCAGAC ATAGCTGCTT CAGTGCCCCT TTTCTCTCTG CTAGATGGAT    1800

GTTGATGCAC TGGAGGTCTT TTAGCCTGCC CTTGCATGGC GCCTGCTGGA GGAGGAGAGA    1860

GCTCTGCTGG CATGAGCCAC AGTTTCTTGA CTGGAGGCCA TCAACCCTCT TGGTTGAGGC    1920

CTTGTTCTGA GCCCTGACAT GTGCTTGGGC ACTGGTGGGC CTGGGCTTCT GAGGTGGCCT    1980

CCTGCCCTGA TCAGGGACCC TCCCCGCTTT CCTGGGCCTC TCAGTTGAAC AAAGCAGCAA    2040

AACAAAGGCA GTTTTATATG AAAGATTAGA AGCCTGGAAT AATCAGGCTT TTTAAATGAT    2100

GTAATTCCCA CTGTAATAGC ATAGGGATTT TGGAAGCAGC TGCTGGTGGC TTGGGACATC    2160

AGTGGGGCCA AGGGTTCTCT GTCCCTGGTT CAACTGTGAT TTGGCTTTCC CGTGTCTTTC    2220

CTGGTGATGC CTTGTTTGGG GTTCTGTGGG TTTGGGTGGG AAGAGGGCAA TCTGCCTGAA    2280

TGTAACCTGC TAGCTCTCCG AAGGCCCTGC GGGCCTGGCT TGTGTGAGCG TGTGGACAGT    2340

GGTGGCCGCG CTGTGCCTGC TCGTGTTGCC TACATGTCCC TGGCTGTTGA GGCGCTGCTT    2400

CAGCCTGCAC CCCTCCCTTG TCTCATAGAT GCTCCTTTTG ACCTTTTCAA ATAAATATGG    2460

ATGGCGAGCT CCTAGGCCTC TGGCTTCCTG GTAGAGGGCG GCATGCCGAA GGGTCTGCTG    2520

GGTGTGGATT GGATGCTGGG GTGTGGGGGT TGGAAGCTGT CTGTGGCCCA CTTGGGCACC    2580

CACGCTTCTG TCCACTTCTG GTTGCCAGGA GACAGCAAGC AAAGCCAGCA GGACATGAAG    2640

TTGCTATTAA ATGGACTTCG TGATTTTTGT TTTGCACTAA AGTTTCTGTG ATTTAACAAT    2700

AAAATTCTGT TAGCCAGAAA AAAAAAAAAA AAAAAAAAA                          2740
```

(2) INFORMATION FOR SEQ ID NO:5:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:5:

```
Tyr Lys Glu Val Thr Lys Leu Ile Asp Asn Asn Lys Thr Glu Lys Glu
 1               5                  10                  15

Ile Leu
```

(2) INFORMATION FOR SEQ ID NO:6:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Cys Gln Phe Val Met Asn Lys Phe Ser Glu Leu Ile Val Asn Asn Ala
 1               5                  10                  15

Thr Glu Glu Leu Leu Tyr
             20
```

(2) INFORMATION FOR SEQ ID NO:7:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Cys Gln Leu Val Asn Arg Lys Leu Ser Glu Leu Ile Ile Asn Asn Ala
 1               5                  10                  15
Thr Glu Glu Leu Leu
            20
```

(2) INFORMATION FOR SEQ ID NO:8:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Cys Glu Tyr Val Val Lys Lys Val Met Leu Leu Ile Asp Asn Asn Arg
 1               5                  10                  15
Thr Glu Glu Lys Ile Ile
            20
```

(2) INFORMATION FOR SEQ ID NO:9:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Cys Glu Phe Val Val Lys Glu Val Ala Lys Leu Ile Asp Asn Asn Arg
 1               5                  10                  15
Thr Glu Glu Glu Ile Leu
            20
```

(2) INFORMATION FOR SEQ ID NO:10:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 21...21
        (D) OTHER INFORMATION: Xaa=I or L (xi) SEQUENCE DESCRIPTION: SEQ ID NO:10:

```
Cys Xaa Xaa Xaa Val Xaa Xaa Xaa Xaa Leu Ile Xaa Asn Asn Xaa
 1               5                  10                  15
Thr Glu Xaa Xaa Xaa Xaa
```

-continued

```
(2) INFORMATION FOR SEQ ID NO:11:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (ix) FEATURE:

(xi) SEQUENCE DESCRIPTION: SEQ ID NO:11:

Cys Lys Asp Val Val Thr Ala Ala Gly Asp Met Leu Lys Asp Asn Ala
 1               5                  10                  15

Thr Glu Glu Glu Ile Leu
                20
```

USE OF PROSAPOSIN AND PEPTIDES OBTAINED THEREFROM FOR TREATMENT OF NEURAL DEGENERATION

This application is a continuation of application Ser. No. 08/958,970, filed Oct. 28, 1997, now abandoned, which is a continuation of application Ser. No. 08/483,146, filed Jun. 7, 1995, now U.S. Pat. No. 5,696,080, which is a divisional of application Ser. No. 08/100,247, filed Jul. 30, 1993 now U.S. Pat. No. 5,571,787, the entire contents of which are hereby incorporated by reference.

GOVERNMENT SUPPORT

This research was supported by National Institutes of Health Grant NS 08682. The government may have certain rights in this invention.

FIELD OF THE INVENTION

This invention discloses the utilization of prosaposin, or fragments thereof, as a cytokine, growth factor or neurotrophin. More specifically, prosaposin may be a neurotrophic factor for populations of neurons for which neurotrophins have yet to be identified.

BACKGROUND OF THE INVENTION

Prosaposin, a 70 kilodalton glycoprotein, is the precursor of a group of four small heat-stable glycoproteins which are required for hydrolysis of glycosphingolipids by lysosomal hydrolases (Kishimoto et al., (1992) *J. Lipid Res.*, 33: 1255–1267) Prosaposin is proteolytically processed in lysosomes to generate saposins A, B, C, and D which exist as four adjacent tandem domains in prosaposin (O'Brien and Kishimoto, (1991) *FASEB J.*, 5: 301–308) All four saposins are structurally similar to each other, including the placement of six cysteines, a glycosylation site and conserved proline residues.

Unprocessed prosaposin also exists as an integral membrane protein and a secreted protein which is present in human milk, cerebrospinal fluid and seminal plasma. The presence of high concentrations of unprocessed prosaposin in the central nervous system indicates that it may play a significant role in addition to activation of lysosomal hydrolases.

Prosaposin binds membrane lipids called glycosphingolipids which are sphingolipids consisting of a carbohydrate head group and two hydrocarbon chains; a fatty acid and a sphingosine derivative. Glycosphingolipids are important components of the myelin sheath, a structure which protects and insulates nerve fibers. Demyelination is a defect common to a number of central nervous system disorders, the most common being multiple sclerosis (MS). MS, a chronic disorder which may lead to total disability, is characterized by damage to the myelin sheath leaving the axons mostly intact. It is currently believed that autoimmune mechanisms, perhaps virally-induced, may play a role in development of the disease. There is currently no effective treatment for MS. Other central nervous system disorders involving demyelination include acute disseminated encephalomyelitis, amyotrophic lateral sclerosis, acute necrotizing hemorrhagic leukodystrophy, progressive multifocal leukoencephalitis, metachromatic leukodystrophy and adrenal leukodystrophy. An example of a demyelinating disease of the peripheral nervous system is Guillain-Barré syndrome (*Pathologic Basis of Disease*, Robbins, S. L. and Cotran, R. S., eds, W. B. Saunders, Philadelphia, (1979), pp. 1578–1582).

Post-polio syndrome is characterized by muscle fatigue and decreased endurance with accompanying muscle weakness and atrophy. The disease is believed to be caused in part by the same type of spinal cord motor neurons that are damaged in amyotrophic lateral sclerosis.

Peripheral nerve injuries and peripheral neuropathies, such as those resulting from diabetes or chemotherapy, comprise the most prevalent peripheral nervous system disorders (see Table 1) Current treatments for peripheral nerve disorders only treat the symptoms, not the cause of the disease.

TABLE 1

| Disease | No. of U.S. patients |
| --- | --- |
| Amyotrophic Lateral Sclerosis | 30,000 |
| Spinal Muscular Atrophy | 50,000 |
| Post-Polio Syndrome | 250,000 |
| Guillain-Barré Syndrome | 20,000 |
| Muscular Dystrophies | 175,000 |
| Peripheral Neuropathies | 1,000,000 |
| Peripheral Nerve Injuries | 500,000 |
| Total | 2,150,000 |

Prosaposin binds glycosphingolipids such as gangliosides, cerebrosides and sulfatides with high affinity and facilitates their transfer from micelles to membranes (Sueda, et al. (1993) *J. Biol. Chem.* in press; Hiraiwa et al., (1992) *Proc. Natl. Acad. Sci. USA.*, 89: 11254–11258). Gangliosides contain one or more sialic acid residues and are most abundant in the plasma membrane of neurons where they constitute approximately 6% of the total lipid mass. Although the function of gangliosides is largely unknown, they have been implicated in the stimulation of neuronal differentiation, neuritogenesis and nervous system repair.

Neurotrophins may be defined as those proteins capable of affecting the survival, target innervation and/or function of neuronal cell populations (Barde, (1989) *Neuron*, 2: 1525–1534). The efficacy of neurotrophins both in vitro and in vivo has been well-documented. The most well-characterized of such proteins is nerve growth factor (NGF) which is synthesized by target cells of sympathetic and sensory neurons and acts as a trophic factor for forebrain cholinergic, peripheral and sensory neurons (Hefti et al., (1989) *Neurobiol. Aging*, 10: 515–533). In vivo experiments indicate that NGF can reverse naturally-occurring as well as physical traumatic injuries to peripheral nerves. For example, local application of NGF has been shown to prevent the atrophy of sensory ganglia resulting from transection of the sciatic nerve in adult rats (Rich et al., (1987) *J. Neurocytol.*, 16: 261–268). In addition, NGF plays a role in the neural regenerative process since it enhances neurite extension of developing sympathetic and sensory neurons (Purves et al., (1988) *Nature*, 336: 123–128). Moreover, since NGF supports the function of forebrain cholinergic neurons which are lost in Alzheimer's patients, this indicates that NGF may have a clinical use in treatment of this disease (Hefti et al., (1989) *Neurobiol. Aging*, 10: 515–533).

Brain-Derived Neurotrophic Factor (BDNF) is synthesized in the central nervous system and is a trophic factor for peripheral sensory neurons, dopaminergic neurons of the substantia nigra, central cholinergic neurons and retinal ganglia (Henderson et al., (1993) *Restor. Neurol. Neurosci.*, 5: 15–28). BDNF has also been shown to prevent normally-occurring cell death both in vitro and in vivo (Hofer and Barde, (1988) *Nature,* 331: 261–262).

Since NGF and BDNF share large regions of homology (approximately 50%), degenerate oligonucleotide primers corresponding to four of these regions were used in PCR reactions to amplify novel related sequences. A related neurotrophic factor called neurotrophin 3 (NT-3) was cloned (Maisonpierre et al., (1990) *Science,* 247: 1446–1451). NT-3 is found both centrally and peripherally and is capable of promoting survival of sensory and sympathetic neurons, including dorsal root ganglia (DRG) explants.

The three neurotrophins described above have different neuronal specificities. All three neurotrophins induced neurite outgrowth from DRG explants. NGF induces neurite outgrowth from sympathetic ganglia (SG) but not nodose ganglion (NG), whereas BDNF induces neurite outgrowth from NG but not SG. NT-3 promotes neurite outgrowth from NG and to a lesser extent from SG, suggesting a broader specificity than either NGF or BDNF (Lindsay et al., (1991) *Restor. Neurol. Neurosci.,* 2: 211–220).

Ciliary Neurotrophic Factor (CNTF) promotes survival of chicken embryo ciliary ganglia in vitro and was also found to support survival of cultured sympathetic, sensory and spinal motor neurons (Ip et al., (1991) *J. Physiol., Paris,* 85: 123–130). Local administration of this protein to the lesion site of newborn rats has been shown to prevent the degeneration of the corresponding motor neurons. CNTF also rescued motor neurons from developmental cell death (Henderson et al., (1993) *Restor. Neurol. Neurosci.,* 5: 15–28).

Fibroblast Growth Factor (FGF) can also promote in vitro survival of embryonic neurons. Effects have also been observed on neuronal survival after lesion in vivo. FGF apparently acts on a wide variety of neurons (Hefti et al., (1989) *Neurobiol. Aging,* 10: 515–533).

The identification of prosaposin itself as a neurotrophic factor which is present in the cell bodies of large populations of neurons including upper and lower motor neurons, and its ability to induce myelination in mouse cerebellar explants, represent significant new functions for this protein. Additionally, the fact that fragments of prosaposin retain neuritogenic activity has no precedent in the literature. No reports have appeared on the use of small active fragments of the aforementioned neurotrophic factors to promote neuronal survival and differentiation. Prosaposin and its derivatives are therefore believed to have important therapeutic potential in the treatment of neurodegenerative and demyelination disorders.

BRIEF DESCRIPTION OF THE FIGURES

FIG. 2*b* provides a sequence alignment of the active 22-mer human saposin C sequence (SEQ ID NO: 1) with the same sequence from four other species mouse (SEQ ID NO: 6), rat (SEQ ID NO: 7), guinea pig (SEQ ID NO: 8), and bovine (SEQ ID NO: 9). The consensus (completely conserved) residues are indicated below the sequence alignment as SEQ ID NO: 10. The sequence of human saposin A (SEQ ID NO: 11) (which is inactive) in the same region is provided to illustrate the divergence between the sequence of three of the first four residues in the same hydrophilic region (18–29) in saposin A but conservation of the remaining residues.

SUMMARY OF THE INVENTION

Figure 1A:
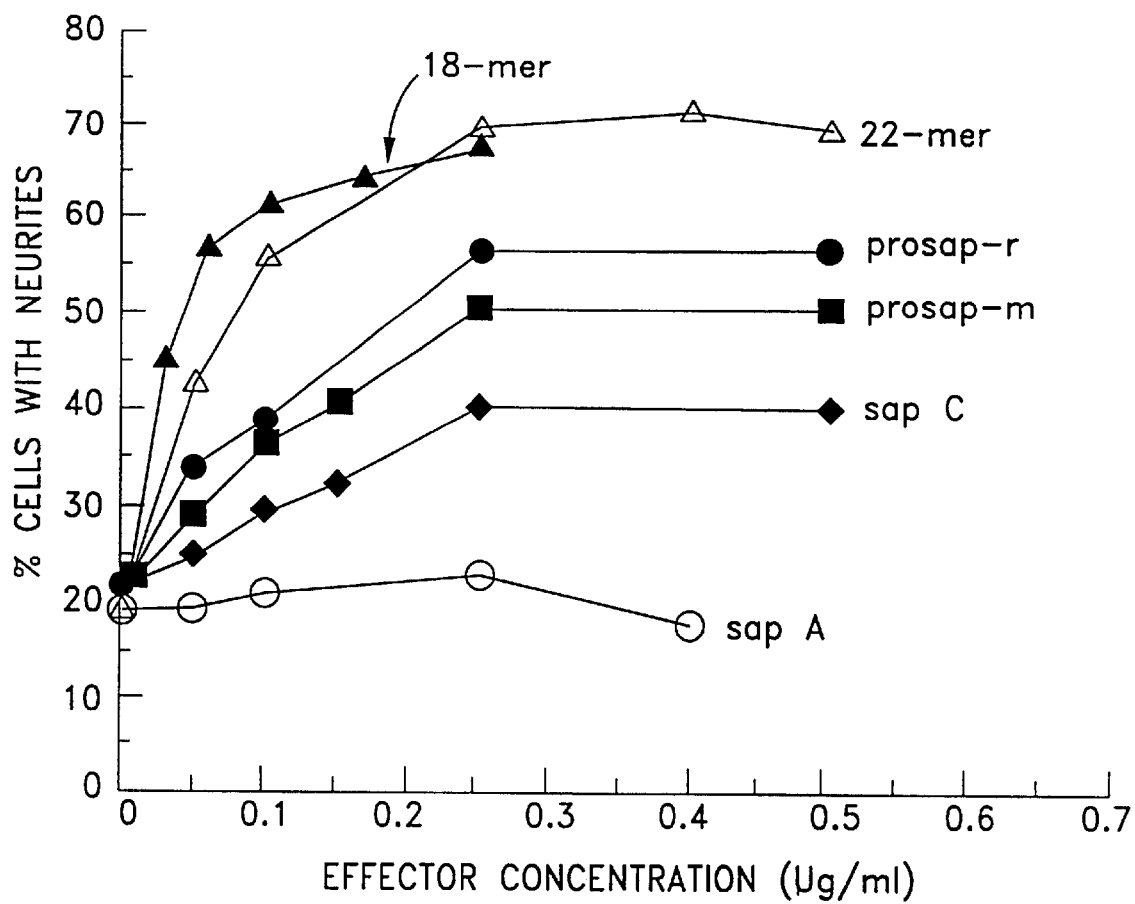
FIG. 1*a* is a graph illustrating the neurite outgrowth response of NS20Y neuroblastoma cells treated with prosaposin, saposin C, active 22-mer peptide (CEFLVKEVTKLIDNNKTEKEIL; SEQ ID NO: 1) and iodine labeled 18 mer over the 0.01–0.5 µg/ml range. The concentration of effector protein, in µg/ml, is shown on the x-axis and the percentage of cells with neurites is shown on the y-axis.

One embodiment of the present invention is a method for stimulating neural cell outgrowth or increased myelination by contacting neuronal cells with a composition including prosaposin or a fragment thereof having the ability to promote increased neural outgrowth or increased myelination activity. Preferably the prosaposin is native. Most preferably the prosaposin is recombinantly produced. The neurotrophic fragment may advantageously be saposin C, a peptide comprising amino acids 8–29 of saposin C, or another peptide containing the same active region. Most preferably, this fragment consists essentially of the active neurotrophic fragment located within amino acids 8–29 of SEQ ID NO 1. Preferably the neuronal cells are either NS20Y, Neuro 2A or N1E115 neuroblastoma cells. These neuronal cells are preferably contacted in vitro and most preferably contacted in vivo. Also within the scope of the invention are cells from mouse cerebellar explants.

Another aspect of the present invention relates to a method for treatment of demyelination disorders in a mammal by identifying a mammal afflicted with the disorder, and administering to the mammal a pharmaceutically effective demyelination inhibiting amount of prosaposin or a neurotrophic fragment thereof. Preferably this fragment is saposin C and the demyelination disorder is either multiple sclerosis, acute disseminated leukoencephalitis, progressive multifocal leukoencephalitis or adrenal leukodystrophy. Preferably, the method of administration is either intramuscular, intradermal, subcutaneous, intracranial, intracerebrospinal or topical in a biologically compatible carrier. Most preferably, the administration is intravenous. Moreover, the prosaposin or fragment thereof may be advantageously enclosed in a lamellar structure.

The invention further comprises a method for halting or slowing the progress of neural or myelin degeneration in neural tissue, by contacting neuronal tissue susceptible to such degradation with prosaposin or an active degradation-inhibiting fragment thereof. Preferably, the fragment is saposin C and the tissue is in vitro. Most preferably the fragment is the neurotrophic peptide and the tissue is in vivo.

Another aspect of the present invention is a method for the treatment of neuronal degenerative diseases of the central or peripheral nervous system, by administering to a mammal suffering from such a disease an amount of a prosaposin fragment effective to retard or halt neuronal degeneration. Most preferably, this fragment includes the neurotrophic activity of the peptide of SEQ ID NO 1 and is able to cross the blood brain barrier. In addition, the administration is intravenous or intradermal. It is envisioned that the disease is a central nervous system disorder including Alzheimer's disease, Parkinson's disease, stroke, post-polio syndrome and amyotrophic lateral sclerosis Further, the invention includes a method for retarding the progress of retinal neuropathy (senile macular degeneration) in a patient by administering to the patient an effective amount of prosaposin or a neurotrophic fragment thereof. Preferably this retinal neuropathy is senile macular degeneration, the patient is a human over the age of 65, and the administration is either topical, intravenous or intraocular.

Another aspect of the present invention is a pharmaceutical composition comprising prosaposin or a neurotrophic fragment thereof in unit dosage form.

Still another aspect of the present invention is a pharmaceutical composition comprising prosaposin or a neurotrophic fragment thereof formulated with a controlled release material.

Finally, the invention includes a neural prosaposin receptor protein in isolated or purified form. Preferably, this receptor protein is the same protein that can be isolated from a P100 plasma membrane fraction by affinity purification using a neurite growth-inducing peptide contained within the saposin C sequence linked to a solid support, and has a molecular weight of approximately 20 kDa.

DETAILED DESCRIPTION OF THE INVENTION

This invention discloses our discovery that prosaposin, saposin C or a peptide comprising amino acids 8–29 of saposin C can be used to stimulate neurite outgrowth and to promote increased myelination.

Prosaposin or its derivatives possess significant therapeutic applications in promoting functional recovery after toxic, traumatic, ischemic, degenerative and inherited lesions to the peripheral and central nervous system. In addition, prosaposin or its derivatives may be used to counteract the effects of demyelinating diseases.

Prosaposin and its derivatives are known to be present in many types of neurons, are water soluble (in contrast to glycosphingolipids) and are less immunogenic than ganglioside micelles since for therapy in humans the human sequence will be used which will not elicit an immune response.

Human prosaposin has the amino acid sequence set forth in SEQ ID NO:2. Saposin C has the amino acid sequence set forth in SEQ ID NO:3. The human cDNA sequence for prosaposin is set forth in SEQ ID NO:4. An active 18-mer fragment derived from the active 22-mer fragment (SEQ ID NO: 1) is set forth as SEQ ID NO: 5.

As will be discussed in more specific detail in the Examples, prosaposin, saposin C and amino acids of saposin C that include at least amino acids 8–29 of SEQ ID NO: 3 A are active as neurotrophic factors. In addition, a peptide including at least amino acids 12–29 (with a tyrosine substituted for valine at position 12A SEQ ID NO: 5) is also an active neurotrophic factor. Similar active peptides, also within the scope of this invention, can be prepared and screened as described herein (See Example 2). These proteins and peptides stimulate the outgrowth of neurites, promote myelination and prevent programmed cell death in neuronal tissues.

One aspect of the present invention is a method for facilitating outgrowth of neurites in differentiated or undifferentiated neural cells. This method requires administration of an effective, neurite-outgrowth facilitating amount of prosaposin, saposin C, or the 18 or 22 amino acid fragment thereof to the cells in question. A typical minimum amount of prosaposin for the neurotrophic factor activity in cell growth medium is usually at least about $1.4 \times 10^{-11}$ M, or about 10 ng/ml. This amount or more of saposin C or its active 18 or 22 amino acid fragments may also be used. Usually concentrations in the range of 0.1 $\mu$g/ml to about 10 $\mu$g/ml of any of these materials will be used. Effective amounts for any particular tissue can be determined in accordance with Example 1.

The neural cells can be treated in vitro or ex vivo by directly administering the neurotrophic factor of the present invention to the cells. This can be done, for example, by culturing the cells in growth medium suitable for the particular cell type followed by addition of the neurotrophic factor to the medium.

When the cells to be treated are in vivo, typically in a vertebrate, preferably a mammal or a bird, the composition can be administered to the cells to be treated by one of several techniques. Most preferably, the composition can be injected directly into the blood in sufficient quantity to give the desired concentration of neurotrophic factor since an iodinated 18-mer peptide consisting of amino acids 12–29 of the 22-mer with a substitution of tyrosine for valine at amino acid 12 (M.W=2000) crosses the blood brain barrier and enters the central nervous system as described in Example 7 (see Banks et al., (1992) *Peptides*, 13: 1289–1294). The uptake by the brain was approximately 0.03% which is in the midrange of values for peptides of that approximate size which will cross the blood brain barrier. This is the only neurotrophic factor so far described which will cross the blood brain barrier when administered intravenously.

Direct intracranial injection or injection into the cerebrospinal fluid may also be used in sufficient quantities to give the desired local concentration of neurotrophin. In both cases, a pharmaceutically acceptable injectable carrier of well known type can be used. Such carriers include, for example, phosphate buffered saline (PBS). Alternatively, the composition can be administered to peripheral neural tissue by direct local injection or by systemic administration. Various conventional modes of administration are contemplated, including intravenous, intramuscular, intradermal, subcutaneous, intracranial, epidural, topical and oral administration.

The composition can be packaged and administered in unit dosage form such as an injectable composition or local preparation in a dosage amount equivalent to the daily dosage administered to a patient or as a controlled release composition. A septum sealed vial containing a daily dose of the active ingredient in either PBS or in lyophilized form is an example of a unit dosage.

Since the molecular weight of the active 22-mer is approximately 2600, and an iodinated 18-mer contained within this sequence will cross the blood brain barrier, then the 22-mer will also most likely cross and enter the central nervous system (Banks et al., (1992) *Peptides*, 13: 1289–1294). Appropriate daily systemic dosages based on the body weight of the vertebrate are in the range of from about 10 to about 100 $\mu$g/kg, although dosages from about 0.1 to about 1000 $\mu$g/kg are also contemplated. Daily dosages of locally administered material will be about an order of magnitude less. Oral administration may be possible if the peptide is stable to gastrointestinal degradation and readily absorbed.

In one preferred embodiment of the invention, the neurotrophic factor is administered locally to the neural cells in vivo by implantation of the material. For example, polylactic acid, polygalactic acid, regenerated collagen, multilamellar liposomes and many other conventional depot formulations comprise bioerodible or biodegradable materials that can be formulated with biologically active compositions. These materials, when implanted, gradually break down and release the active material to the surrounding tissue. The use of bioerodible, biodegradable and other depot formulations is expressly contemplated in the present invention. Infusion pumps, matrix entrapment systems, and combination with transdermal delivery devices are also contemplated.

The neurotrophic factors of the present invention may also advantageously be enclosed in micelles or liposomes.

Liposome encapsulation technology is well known. Liposomes may be targeted to specific tissue, such as neural tissue, through the use of receptors, ligands or antibodies capable of binding the targeted tissue. The preparation of these formulations is well known in the art (i.e., Radin and Metz, (1983) *Methods Enzymol.*, 98: 613–618).

There are currently no available pharmaceuticals able to promote full functional regeneration and restoration of structural integrity of neural systems. This is particularly true of the central nervous system. Regeneration of peripheral nerves through use of neurotrophic factors is a more immediately demonstrable goal. Such treatment is within the scope of this invention. Moreover, neurotrophic factors can be therapeutically useful in the treatment of neurodegenerative diseases associated with the degeneration of neural populations or specific areas of the brain. The principal cause of Parkinson's disease is the degeneration of dopaminergic neurons of the substantia nigra. Since antibodies against prosaposin immunohistochemically stain the dopaminergic neurons of the substantia nigra in human brain sections, prosaposin and its active fragments may be therapeutically useful in the treatment of Parkinson's disease.

It has long been believed that in order to reach neuronal populations in the brain, neurotrophic factors would have to be administered intracerebrally, since these proteins do not cross the blood-brain barrier. However, as previously mentioned, the active iodinated 18-mer will cross and the active 22-mer will most likely cross this barrier and would thus be administered intravenously. Other neuronal populations, such as motor neurons, would also be treated by intravenous injection, although direct injection into the cerebrospinal fluid is also envisioned as an alternate route.

Cells may be treated to facilitate myelin formation or to prevent demyelination in the manner described above, both in vitro, ex vivo and in vivo. There are several diseases that result in demyelination of nerve fibers including multiple sclerosis, acute disseminated leukoencephalitis, progressive multifocal leukoencephalitis, metachromatic leukodystrophy and adrenal leukodystrophy. These diseases can be treated, and the progression of the demyelination can be slowed or halted, by administration of the neurotrophic factors of the present invention to the cells affected by the disease.

The compositions of the present invention can be used in vitro as research tools for studying the effects of neurotrophic factors and myelin facilitating materials. However, more practically, they have an immediate use as laboratory reagents and components of cell growth media in order to better enable growth of neural cells in vitro.

The prosaposin used in the present invention may be obtained from various sources, and may be, for example, naturally occurring protein isolated from human milk or seminal plasma or recombinant human prosaposin purified from spent media of *Spodoptera frugiperda* (Sf9) cells infected with a baculovirus expression vector containing full-length cDNA for human prosaposin as described (Dewji et al., (1987) *Proc. Natl. Acad. Sci. USA*, 84: 8652–8656). O'Brien et al., (1988) *Science*, 241: 1098–1101); Hiraiwa et al., (1993) *Arch. Biochem. Biophys.*, 304, 110–116). Saposin C is isolated in pure form from spleens of patients with Gaucher disease, a lysosomal storage disorder (Morimoto et al., (1990) Proc. *Natl. Acad. Sci. USA*, 87: 3493–3497). Saposin C (80 amino acids) can also be chemically synthesized and refolded (Weiler et al., (1993) *J. Mol. Neurosci.*, in press).

The peptides corresponding to sequences within saposin C may be synthesized using an automated solid-phase protocol on an Applied Biosystems Model 430 peptide synthesizer. After synthesis, peptides 1–40, 41–82, 1–27, 13–34 and 21–48 are desalted on a Sephadex G-75 column prior to use.

EXAMPLE 1

Effect of Prosaposin, Saposins and NGF on NS20Y Neurite Outgrowth

NS20Y neuroblastoma cells were grown in Dulbecco's Modified Eagle Medium (DMEM) containing 10% fetal calf serum (FCS) and 1 mM sodium pyruvate. Cells were removed with trypsin and plated in 30 mm petri dishes onto glass coverslips. After 20–24 hours the medium was replaced with DMEM containing 0.5% fetal calf serum plus effector proteins. Cells were cultured for another 24 hours, washed with phosphate buffered saline (PBS) and fixed with Bouin's solution (saturated aqueous picric acid/formalin/acetic acid 15:5:1) for 30 minutes. Fixative was removed with PBS and neurite outgrowth was scored under a phase contrast microscope. Cells exhibiting one or more clearly defined neurites equal to or longer than one cell diameter were scored as positive. At least 200 cells were scored in different portions of each dish to determine the percentage of neurite bearing cells and assays were performed in duplicate.

A dose-response curve (FIG. 1a) demonstrated that prosaposin promoted reversible neurite outgrowth in NS20Y neuroblastoma cells. The lowest concentration for activity was $1.4 \times 10^{-11}$ M (10 ng/ml) which is in the effective concentration range of other neurotrophins. When prosaposin was removed, retraction of neurite outgrowth was complete at 36 hours, demonstrating that its continual presence is necessary in order to maintain neurite outgrowth. In addition, saposin C was the sole fragment of prosaposin found to possess neuritogenic activity, as did the 22-mer and iodinated 18-mer peptides derived from the saposin C sequence.

Figure 1B:
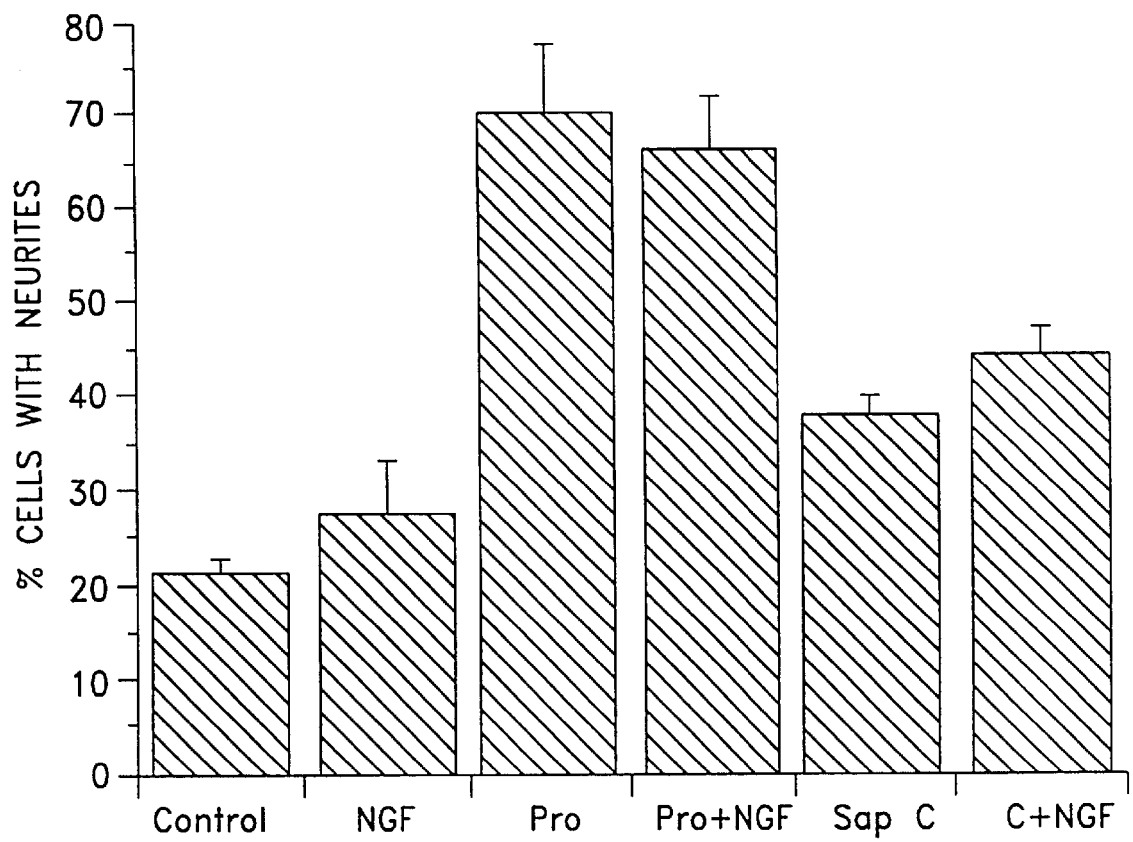
FIG. 1*b* is a bar graph showing the effect of 5 µg/ml NGF on neurite outgrowth in prosaposin and saposin C treated NS20Y cells. The y-axis indicates the percentage of cells with neurites.

Since nerve growth factor (NGF) acts on a variety of cell types, we wanted to determine whether it was involved in prosaposin-mediated outgrowth in neuroblastoma cells. NGF by itself had no effect on neurite outgrowth in NS20Y cells and did not augment the prosaposin response (FIG. 1b). When 5'-methyladenosine (MeSAdo), which specifically inhibits NGF-induced neuritogenesis in PC12M pheochromocytoma cells was added, MeSAdo did not inhibit prosaposin-induced NS20Y neurite outgrowth. Additionally, prosaposin failed to stimulate neurite outgrowth from NGF-responsive PC12M cells at high concentrations (2 mg/ml). Since NS20Y cells are not NGF responsive, this indicates that the NGF response and the prosaposin response are different.

Figure 2A:
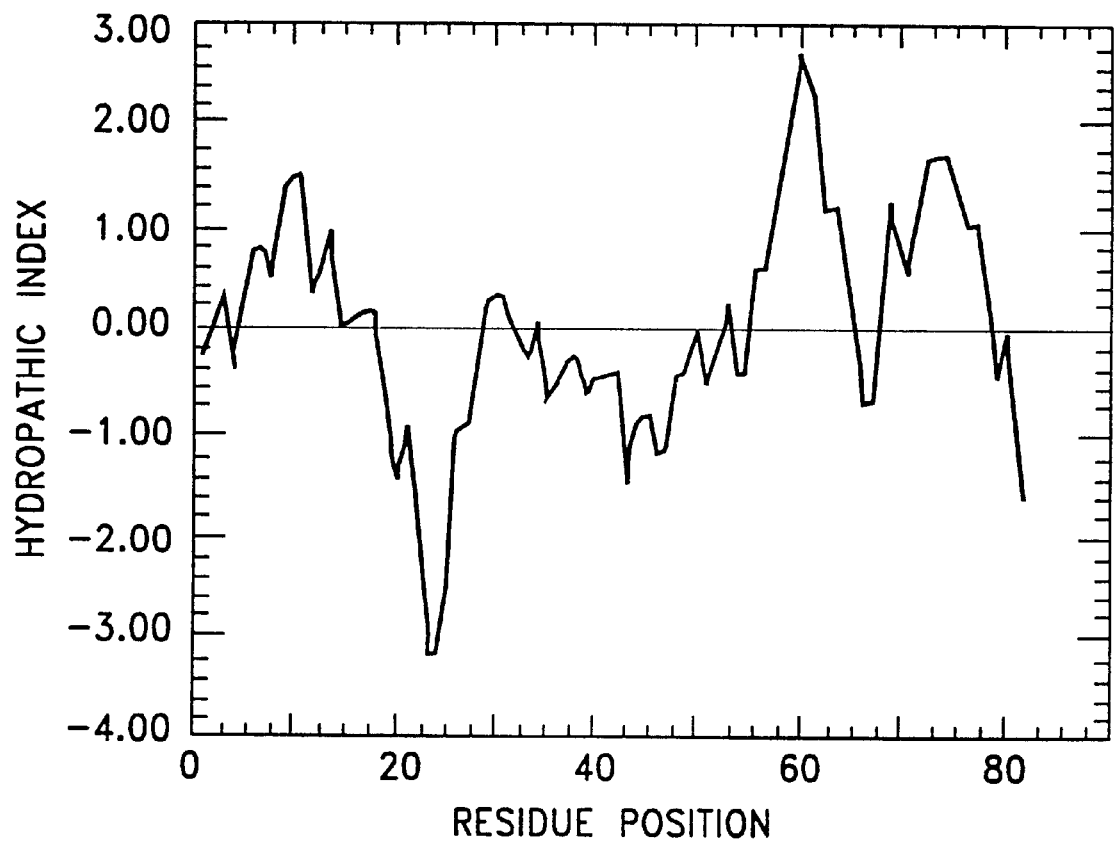
FIG. 2*a* shows a hydropathy plot of the human saposin C sequence. The amino acid residue position is shown on the x-axis and the hydropathic index is shown on the y-axis.

A set of synthetic peptides from different regions of saposin C was utilized to further define the active sequence. An amino terminal peptide (1–40) was active and a carboxy terminal peptide (41–82) was inactive. Testing of four more peptides (Table 2) further narrowed the active sequence to a region between residues 8–29, the most hydrophilic region in the saposin C domain (FIG. 2a) which also contains the single glycosylation site (Asn 22). Higher concentrations of the active 22-mer (residues 8–29) were required for activity but the extent of neurite outgrowth was greater than with prosaposin or saposin C (FIG. 1a). The sequence between residues 18 and 29 is highly conserved (FIG. 2b). Interestingly, human sanosin A is newly identical to saposin C in this region except for the first four residues, indicating that the active sequence requires the presence of leucine 18 and asparagines at residues 21 and 22 or both.

TABLE 2

Neurite outgrowth response of NS20Y cells treated with human saposin C, saposin A and synthetic peptides from the human saposin C domain at 5 µg/ml. The dose response curve for peptide 8–29 (active 22 mer) is given in FIG. 1a.

| Peptide Added (5 µg/ml) | % Neurites after 24 hours |
| --- | --- |
| Saposin C | 40% |
| 1–40 | 42% |
| 41–82 | 17% |
| 1-27 | 46% |
| 13–34 | 50% |
| 21–48 | 18% |
| 8–29 | 56% |
| Saposin A | 20% |
| None | 18% |

To test whether gangliosides were involved in the response, a prosaposin-ganglioside GM1 complex (4:1) was generated by a method well known in the art. When tested in the neurite outgrowth assay, the complex had negligible activity. The same result was obtained with a ganglioside GM3-saposin C complex. This indicated that the neuritogenic effect was not the result of ganglioside transport, but was instead due to the prosaposin and saposin C, respectively.

In order to determine whether prosaposin or its fragments would have an effect on neurite outgrowth in nontransformed cells, newborn mouse cerebellar explants were used as described in the following example:

EXAMPLE 2

Effect of Prosaposin and Its Active Fragments on Neurite Outgrowth in Mouse Cerebellar Explants Newborn mouse cerebellar explants were prepared according to Satomi (*Zool. Sci.* 9, 127–137 (1992)). Neurite outgrowth and myelination were observed over 22 days in culture, during the period when the newborn mouse cerebellum normally undergoes neuronal differentiation and myelination begins. Prosaposin (5 µg/ml) and saposins A, B and C (10 µg/ml) were added on the second day after preparation of the explants (three control and three treated explants) and outgrowth of neurites and myelination were assessed under a bright field microscope with a video camera. On the eighth day cultures containing prosaposin and saposin C became thinner and more spread out than control cultures. On day 15, the prosaposin and saposin C treated cultures contained many cells with long projections at the periphery of the explant which were less prominent in controls or those treated with saposins A or B. Saposin C treated cultures contained twice as many myelinated axons in the subcortical white matter at 22 days as controls or those treated with saposins A or B. Both the number of myelinated fibers observed visually per optical field and the activity of the myelin marker enzyme CNP were twice the control value. These results demonstrate that the neurotrophic effect of prosaposin and saposin C also occurs in differentiating cerebellum ex vivo. These results further demonstrate the ability of prosaposin and saposin C to induce increased myelination in differentiating cerebellum ex vivo.

Since prosaposin appears to be active at the plasma membrane it should be present in the plasma membranes of responsive cells as shown in the following example:

EXAMPLE 3

Western Blots of Prosaposin and Saposin C from NS20Y Cells

NS20Y cells were grown to confluence in 75 cm flasks in the presence of growth medium. Cells were harvested by scraping and surface membranes were isolated by the zinc ion method of Warren and Glick (1969) using discontinuous gradients of 50, 48, 45, 43, 40 and 35% sucrose; surface membranes localize in the 40 and 43% sucrose fraction. These fractions, as well as the infranatant and supernatant fractions bounding them, were electrophoresed on 10% SDS polyacrylamide gels along with the whole cell extracts, transferred to nitrocellulose filters, and probed with a monoclonal antibody to saposin C by methods well known in the art.

Examination of Western blots revealed that prosaposin, migrating as a 68 kDa band on SDS polyacrylamide gels, was localized to surface membrane fractions from both NS20Y and Neuro 2A cells. Mature saposin C and intermediate molecular weight saposin derivatives were minor components of the membrane fractions but were abundant in the whole cell extract. This demonstrates that prosaposin is located in the plasma membrane of responsive cells.

In order to localize prosaposin histochemically, neuroblastoma cell lines were immunostained with a prosaposin-specific antibody (JP-1) as illustrated in the following example:

EXAMPLE 4

Immunohistochemical Localization of Prosaposin

Cells were grown on glass cover slips, washed three times with PBS and fixed with Bouin's solution for one hour at room temperature. Bouin's solution was then rinsed out with 5 washes of PBS and slips were incubated in 30% goat serum, 0.5% Tween 20 in PBS to block nonspecific binding and, after rinsing, were incubated in a 1:100 dilution of IgG purified rabbit JP-1 at 40° C. overnight. After rinsing with PBS containing 0.1% Triton X-100, the preparations were incubated with either peroxidase conjugated goat anti-rabbit IgG (Bio-Rad, 1:2000) or FITC-conjugated goat anti-rabbit IgG (Cappel, 1:2000). After rinsing, peroxidase immunostaining was detected using the imidazole-diaminobenzidine-$H_2O_2$ reaction. Fluorescence immunostaining was detected under a fluorescence microscope using Nofade as a quenching deterrent. Preimmune rabbit IgG (1:100) was used as a control for nonspecific binding. Immunostaining of extended neurites, plasma membranes and growth cones were observed.

A similar methodology was used to immunostain postmortem human brain sections to detect reactive cell types. In frontal cortex, intense staining of the perikarya of large and medium sized Golgi type 1 neurons was observed. The surface of neuronal perikarya and the proximal segment of axons at the hillock region were also strongly stained as were some extended axons. In the cerebellum strong staining of Purkinje and stellate cells was observed, as well as large neurons in the cerebellar nuclei (dentate, emboliform and globose nuclei). Cerebellar granular cells were moderately stained. In the mesencephalon, moderate staining was observed in dopaminergic neurons of the substantia nigra. Large neurons in the red nucleus, neurons in the oculomotor nucleus, the amygdaloid nucleus and ependymal cells lining the lateral ventricle were also moderately stained. In the hippocampus, pyramidal cells and granule cells of the dentate gyrus were strongly stained. In the spinal cord alpha motor neurons were intensely stained. This survey indicated that prosaposin was localized to populations of large neurons including upper and lower motor neurons.

Since all neurotrophins identified thus far exert their effects by binding to a cell surface receptor and initiating a kinase cascade, phosphorylation assays were performed in NS20Y cells treated with prosaposin or its fragments as described in the following example:

EXAMPLE 5

Incorporation of 32P into NS20Y Proteins After Treatment with Prosaposin or Its Active Fragments NS20Y cells were incubated in phosphate-free Hanks' balanced salt solution containing 2.5 µg/ml actinomycin D and 80–100 µCi/ml carrier-free [$^{32}$P]-orthophosphate (New England Nuclear) and effector proteins (0.5–1.0 µg/ml) and incubated for 10–15 minutes at room temperature. Cells were solubilized in SDS-PAGE sample buffer, analyzed by SDS-PAGE and autoradiographed.

Prosaposin, saposin C and SEQ ID NO: 1 were found to stimulate phosphorylation of proteins of 148, 100, 80, 68, 50, 38 and 34 kDa to a greater extent than controls or cells treated with similar concentrations of saposins A, B or D. This 148 kDa protein may be phospholipase C-γ, a protein known to be involved in phospholipid metabolism and which is phosphorylated on tyrosine residues in response to a number of growth factors. Densitometric analysis indicated a 3–5 fold stimulation of phosphorylation after 10 minutes. Treatment of gels with alkali revealed that the prominent phosphorylated proteins were alkali-resistant, indicating that they contain phosphotyrosine and/or phosphothreonine (located next to praline) residues. These results indicate that prosaposin and its active fragments bind to a cell surface receptor and activate a kinase cascade, similar to other neurotrophins and growth factors.

Since prosaposin-ganglioside GM1 or saposin C-ganglioside GM3 complexes inhibit neuritogenesis, while prosaposin or saposin C alone promote this process, this indicates that gangliosides may abolish neuritogenic activity by masking a receptor binding site on the neurotrophin. In addition, since prosaposin and its active fragments induce tyrosine phosphorylation of cytoplasmic proteins in responsive cells, most likely by activation of a tyrosine kinase(s) similar to cytokines and growth factors, this provides further evidence that a cell surface receptor is involved.

A 20 kDa protein has been identified as the putative receptor for prosaposin as described in the following example:

EXAMPLE 6

Isolation of the Prosaposin Receptor

The putative prosaposin receptor protein was isolated from whole rat brain, rat cerebellum and mouse neuroblastoma cells using the plasma membrane P-100 fraction. Briefly, cells or tissues were solubilized and centrifuged at 14,000 rpm to remove debris. The supernatant was centrifuged at 40,000 rpm for 1 hour at 4° C. The pellet, enriched in plasma membrane, was solubilized in RIPA buffer (10 mM MOPS, pH 7.5, 0.3 M sucrose, 5 mM EDTA, 1% Trasylol, 10 µM leupeptin and 10 µM antipain). This P-100 fraction was applied to an affinity column containing the bound, active 22-mer fragment of saposin C. The column was washed with 0.25 M NaCl to elute loosely-bound proteins followed by 1.0 M NaCl which eluted the putative 20 kDa prosaposin receptor. In addition, it was determined that the 20 kDa protein could be eluted using a 100 fold excess of unbound peptide thus demonstrating specific elution. The 20 kDa protein was approximately 90% pure as judged by SDS-PAGE. The protein was purified to homogeneity using HPLC and eluted at 50% acetonitrile in an acetonitrile/water gradient on a Vydac C4 column.

EXAMPLE 7

In vivo Peptide Uptake by the Central Nervous System

An 18-mer peptide consisting of amino acids 12–29 of saposin C with a tyrosine substituted for valine at position 12 was chemically synthesized on an Applied Biosystems Model 430 peptide synthesizer. The peptide was then radio-iodinated by the lactoperoxidase method and 20×10$^6$ cpm were injected into the auricles of rats. The animals were sacrificed after one hour and 24 hours and the hearts were perfused with isotonic saline in order to remove the blood from the brain. The brain was then counted in a gamma counter in order to determine the percentage of peptide uptake. In addition, in the 24 hour experiment the brain was homogenized and separated into a capillary rich fraction (pellet) and a parenchymal brain fraction (supernatant) after dextran centrifugation (Triguero et al., (1990) *J. Neurochem.*, 54: 1882–1888). This method allows for the discrimination between radiolabelled peptide within blood vessels and that within the brain. In the 24 hour experiment, 0.017% of the injected peptide was detected in whole brain, 75% of the label was in the parenchymal fraction and 25% was in the capillary fraction. At 1 hour 0.03% of the injected dose was present in whole brain.

EXAMPLE 8

Use of Prosaposin and Its Active Fragments in Treating Traumatic Ischemic Lesions to the CNS In vivo Rats with traumatic lesions to the spinal cord receive direct or intravenous administration of prosaposin or its active fragments in the 10 ng–10 mg/ml range in a sterile saline solution or in a depot form to enable slow release. The same number of animals receive only saline. After surgical partial transection of the spinal cord or a crush injury, prosaposin or a neurotrophic fragment thereof is directly injected into the lesion site using the same dose range (control animals receive saline injections) and improvement is assessed by gain of motor neuron function (i.e., increased limb movement). The treatments continue until no further improvement occurs. Since prosaposin and its active fragments are very water-soluble, no special delivery system for the preparation is required. Injection of the 18 or 22 amino acid fragments is preferred since there is less chance of degradation and diffusion will be greater. Additionally, this fragment can be chemically synthesized in large quantities.

EXAMPLE 9

Use of Prosaposin and Its Active Fragments in Treating Demyelination Disorders

Patients diagnosed with early stage MS (or other demyelination disorder) are given the active 18 or 22-mer fragment (in saline) by direct intravenous injection or injection into the cerebrospinal fluid using the same dose range as in Example 7. Control patients receive only saline. The treatment is administered weekly or monthly and any improvement is assessed by increased muscle strength, musculoskeletal coordination, and assessing myelination by magnetic resonance imaging.

EXAMPLE 10

Use of Prosaposin or Its Active Fragments in Treating Retinal Neuropathy

Retinal neuropathy, an ocular neurodegenerative disorder leading to loss of vision in the elderly, is believed to be a disorder treatable by prosaposin or its active fragments. Prosaposin or its active neurotrophic fragments are administered either topically, systemically or intraocularly in an amount sufficient to produce a local concentration of neurotrophin of about 10 ng/ml to about 10 mg/ml. The administration is continued weekly until visual loss is slowed or no further increase in vision is noticed.

What is claimed is:

1. A method for increasing the survival of retina in a patient in need thereof comprising the step of administering to the patient an amount of prosaposin or a neurotrophic fragment comprising amino acids 8–29 of SEQ ID NO:3, wherein said amount is sufficient to increase the survival of the retina.

2. The method of claim 1 wherein said patient is a human over the age of 65.

3. The method of claim 1 wherein said administering step is selected from the group consisting of: topical, intravenous, intraocular and oral.

4. The method of claim 1, wherein the retina has macular degeneration.

* * * * *